United States Patent [19]

Peterson et al.

[11] Patent Number: 4,894,532
[45] Date of Patent: Jan. 16, 1990

[54] OPTICAL FIBER SENSOR WITH LIGHT ABSORBING MOISTURE-SENSITIVE COATING

[75] Inventors: Steven H. Peterson, Murrysville; Alfred R. Pebler, Wilkinsburg; Rajender K. Sadhir, Plum Boro; Henry A. Pearce Jr., Stoneboro; C. Clair Claiborne, Sharpsville, all of Pa.

[73] Assignee: Westinghouse Electric Corp., Pittsburgh, Pa.

[21] Appl. No.: 173,897

[22] Filed: Mar. 28, 1988

[51] Int. Cl.$^4$ .......................... H01J 5/16; H01J 40/14
[52] U.S. Cl. ...................................... 250/227; 73/73; 73/336.5
[58] Field of Search ................. 250/227; 73/29, 336.5, 73/73; 356/135, 136

[56] References Cited

U.S. PATENT DOCUMENTS

| | | | |
|---|---|---|---|
| 3,528,278 | 9/1970 | Sterling | 350/96.1 |
| 4,050,895 | 9/1977 | Hardy et al. | 250/227 |
| 4,221,962 | 9/1980 | Black et al. | 73/73 |
| 4,634,856 | 1/1987 | Kirkham | 250/227 |
| 4,641,524 | 2/1987 | Tarvin | 73/336.5 |
| 4,652,323 | 3/1987 | Butt | 350/96.23 |
| 4,696,796 | 9/1987 | Oka et al. | 73/336.5 |

FOREIGN PATENT DOCUMENTS

| | | | |
|---|---|---|---|
| 2420594 | 11/1975 | Fed. Rep. of Germany . | |
| 0111423 | 7/1982 | Japan | 356/51 |
| 1264239 | 11/1986 | Japan | 356/51 |

OTHER PUBLICATIONS

R. K. Sadhir and H. E. Saunders, "Deposition of Conducting Thin Films of Organometallic Monomers by Plasma Polymerization", J. Vac. Sci., Tech. A3(6) 2093 (1985).

R. K. Sadhir and H. E. Saunders, "Protective Thin Film Coatings by Plasma Polymerization," Semiconductor International 8(3), 110, (1985).

S. M. Angel, "Optrodes Chemically Selective Fiber-Optic Sensors", *Spectroscopy*, vol. 2, No. 4, pp. 38-48, Apr. 1987.

R. K. Sadhir and W. J. James, "Synthesis and Properties of Conducting Films by Plasma Polymerization of Tetramethyltin", ACS Symposium Series No. 242, Polymers in Electronics, Chapter 42, pp. 533 (1984), Edited by T. Davidson.

R. K. Sadhir, H. E. Sanders and W. J. James, "Plasma Polymerized Organometallic Thin Films: Preparation and Properties", ACS Symposium Series No. 242, Polymers in Electronics, Chapter 43, pp. 555 (1984), Edited by T. Davidson.

*Primary Examiner*—David C. Nelms
*Assistant Examiner*—Michael Messinger

[57] ABSTRACT

An optical fiber moisture sensor is prepared by coating an optical fiber with a thin film of plasma polymerized hexamethyldisiloxane and ammonia, approximately 1-2 $\mu$m thick. The light transmission characteristics of such a coated optical fiber change as a function of moisture conditions in an environment to which the coating is exposed. Accordingly, the coated optical fiber may be utilized by sensing changes in moisture conditions in an environment by being placed in the environment, causing light to be transmitted through the fiber and detecting changes in the light transmitted through the fiber as a function of the moisture conditions in the environment.

23 Claims, 5 Drawing Sheets

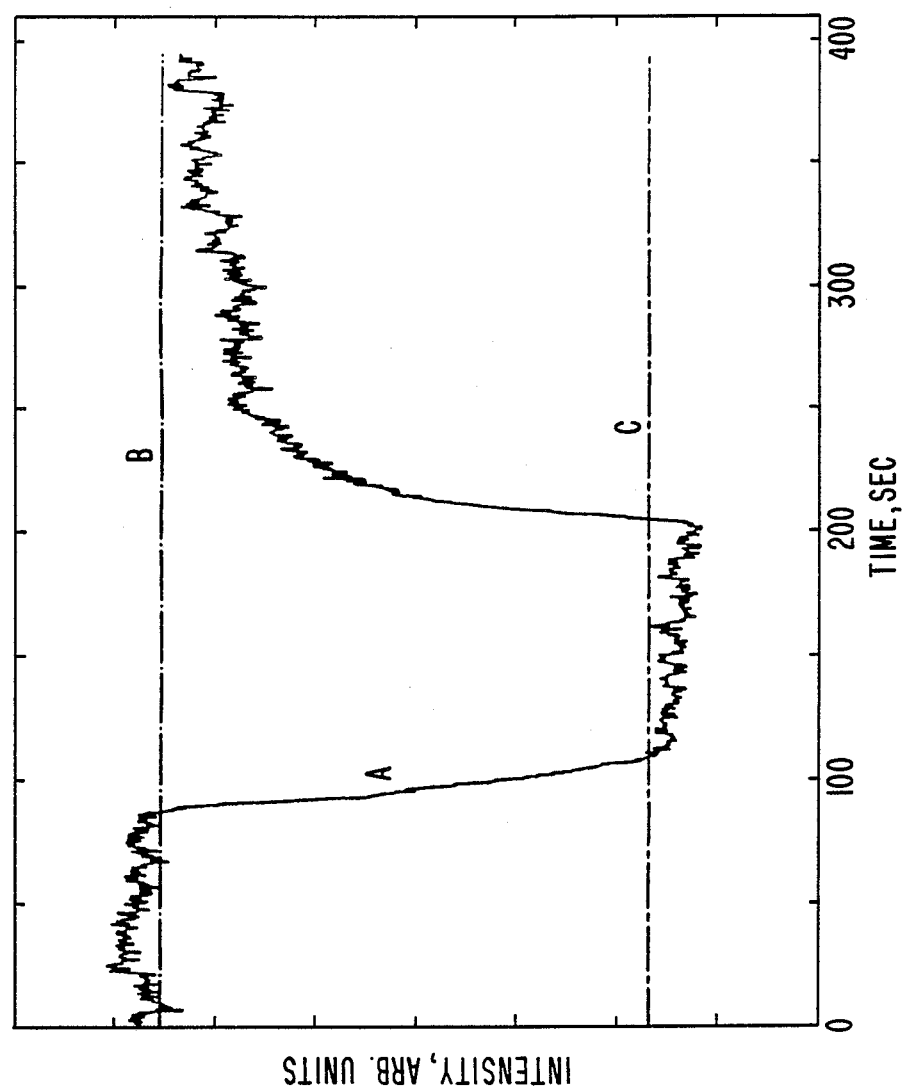

OPTICAL FIBER SENSOR WITH LIGHT ABSORBING MOISTURE-SENSITIVE COATING

BACKGROUND OF THE INVENTION

1. Field of the Invention

The present invention relates to the field of sensors for measuring moisture in an environment and in particular to a method and means for sensing changes in moisture content in an environment utilizing an optical fiber that is sensitive to changes in moisture content.

2. The Prior Art

Sensors are the key component in a wide range of systems used in chemical process control, pollution monitoring, robotics, and chemical warfare agent detection, for example. In response to the development of the need for such systems, advances in sensor technology, and in particular sensors having higher sensitivity and response speed along with reduced size and cost are continually being sought. It has been shown that plasma polymerized thin films deposited from a mixture of hexamethyldisiloxane and ammonia may be useful as sensor membranes for detecting oxidizing gases and moisture. Sensors based on such thin films have exploited the fact that the sheet resistance of the plasma polymerized film decreases gradually with an increase in relative humidity and the fact that such moisture effect is reversible. In one such thin film moisture sensitive detector, having a conductivity read out, the sheet resistance changed from $10^{18}$ to $10^{10}$ $\Omega$ as the relative humidity changed from 0 to 92%. And in such instrument it was shown that the transition between stable readings is rapid.

However, there are a number of applications where it would be desirable to measure moisture, but where conductivity measurement is not practical. An example of such application is in the control of moisture in power transformers with paper-oil insulation. Depending on the operating and ambient conditions, the moisture level in the transformer oil can vary significantly. At present, moisture is determined on batch samples taken from the operating transformer. On-line monitoring of moisture in oil would permit control of moisture build up within desired limits. Another attractive application for a fiber optical moisture sensor is in a hydrogen cooled generator. An on-line moisture sensor would permit signalling of the malfunction or exhaustion of the gas dryer and/or in leakage of ambient air.

Optical fiber sensors have been investigate extensively. And the properties and applications of chemically selective fiber-optic sensors (Optrodes) are presented in an article authored by S.M. Angel and entitled "Optrodes: Chemically Selective Fiber-Optic Sensors" which appeared in Spectroscopy, Vol. 2, No. 4, pp. 38-48, April 1987. Among other advantages, optical fiber sensors have been found to be generally insensitive to electrical interference. Fiber optic chemical sensors have been described using a number of optical phenomena, including absorption across a gap between two fiber ends, fluorescence initiated by light transmitted through an optical fiber and collected by the same fiber, absorbance of light by a substrate at the end of a fiber with observation of the transmitted or reflected light, and a number of other effects. Of particular interest for the present disclosure is the technique of evanescent wave attenuation at the surface of a fiber, whereby the light travelling through the fiber by multiple internal reflections is modulated by the absorption spectrum of the surrounding medium. Sensors exploiting this technique have been employed for detecting color changes in an indicating dye immobilized in a plastic coating on a fiber-optic core in response to pH changes in a solution in which the fiber-optic probe is immersed.

In the past, however, there has been no reported use of optical fibers for sensing moisture.

SUMMARY OF THE INVENTION

The present invention provides a method for sensing changes in moisture condition in an environment. The invention comprises placing a moisture sensitive optical fiber in an environment where changes in moisture conditions are to be sensed, causing light to be transmitted through the fiber and detecting changes in the transmitted light through the fiber as a function of changes in the moisture conditions in the environment. The method of the invention has been facilitated through the provision of a moisture sensitive optical fiber which is prepared by plasma polymerization of hexamethyldisiloxane and ammonia onto an optical fiber. In accordance with the method of the invention, light is caused to be transmitted by emission of light from a stabilized light source. Preferably the transmitted light is emitted from the light source at a wavelength greater than 700 nanometers (nm), and in a specifically preferred form of the invention, the transmitted light is emitted from the light source at a wavelength of about 820 nm. The transmitted light may be pulsed, or chopped to permit synchronous detection and preferably the light is reflected so as to make a double pass through the fiber prior to the detection step.

In another aspect of the invention, an optical fiber moisture sensor is provided. The sensor comprises an optical fiber and a coating on the fiber which is capable of altering the optical transmission characteristics of the fiber as a function of moisture conditions in an environment to which the coating is exposed. The coating may be a polymeric coating and preferably is a plasma polymerized coating made by plasma polymerization of hexamethyldisiloxane and ammonia onto a substrate.

In accordance with the major purpose of the invention, apparatus is provided for sensing changes in moisture conditions in an environment. The apparatus of the invention comprises a moisture sensitive optical fiber, means for mounting the fiber in an environment where changes in moisture condition are to be sensed, means for emitting light to be transmitted through the fiber and means for detecting changes in the transmitted light. In accordance with the invention, the moisture sensitive optical fiber may comprise a transparent substrate and a polymeric coating on the substrate, and in a particularly preferred form of the invention, the coating is prepared by depositing, by plasma polymerization, a thin film from hexamethyldisiloxane and ammonia. The substrate may generally be a fiber core which is 100 to 1000 micrometers (um) in diameter and 10 to 100 centimeters (cm) in length. And in particular, the coating should have a thickness in the range of from about 1 to about 10 um.

BRIEF DESCRIPTION OF THE DRAWINGS

FIGS. 4, 5 and 6 are charts plotting the results of experimentation conducted utilizing the apparatus illustrated in FIG. 1.

DESCRIPTION OF THE PREFERRED EMBODIMENTS

Figures 1, 2:
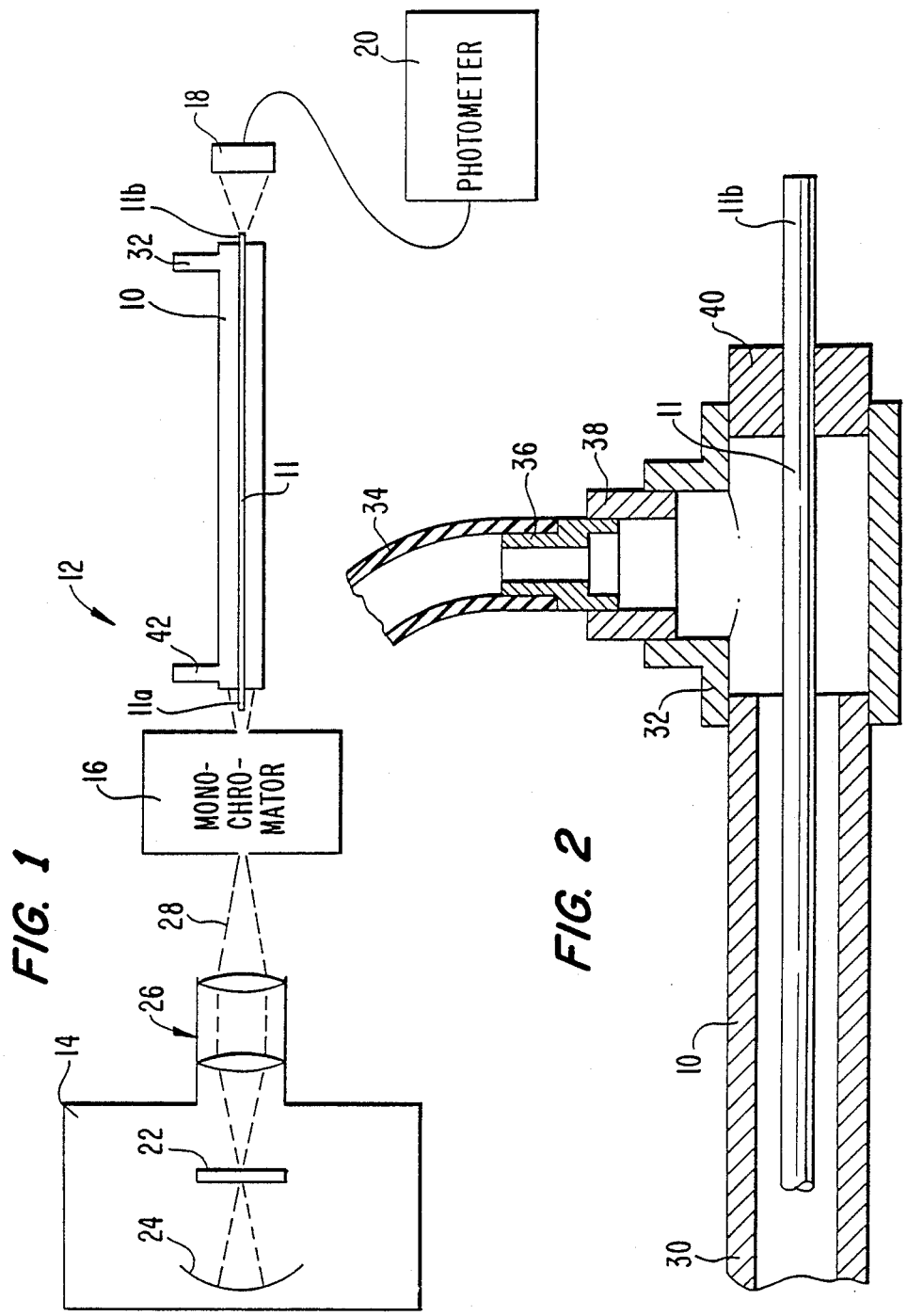
FIG. 1 is a schematic drawing illustrating an optical system used to demonstrate the operation of a fiber-optic moisture probe.
FIG. 2 is an enlarged schematic view illustrating the details of the construction of one end of the flow cell utilized in the apparatus of FIG. 1.

The present invention is directed to the use of an optical fiber moisture sensor which comprises an optical fiber that is coated with a polymeric coating capable of altering the optical transmission characteristics of the fiber as a function of moisture conditions in an environment to which the coating is exposed. It has been discovered, in accordance with the invention, that the polymeric coating may preferably be a plasma polymerized thin film deposited on a fiber core from a mixture of hexamethyldisiloxane and ammonia. The fiber core may take any form known to be useful in connection with fiber-optics generally; however, preferably, for purposes of the present invention, the fiber core should be approximately 100 to 1000 um in diameter and approximately 10 to 100 cm in length. Moreover, the polymeric coating should preferably have a thickness of from about 1 to about 10 um.

Procedures and apparatus for plasma polymerization are generally known and such procedures are described, for example, in the following publications:

R. K. Sadhir and W. J. James, "Synthesis and Properties of Conducting Films by Plasma Polymerization of Tetramethyltin", ACS Symposium Series No. 242, Polymers in Electronics, Chapter 42, pp. 533 (1984), Edited by T. Davidson.

R. K. Sadhir, H. E. Saunders and W. J. James, "Plasma Polymerized Organometallic Thin Films: Preparation and Properties", ACS Symposium Series No. 242, Polymers in Electronics, Chapter 43, pp. 555 (1984). Edited by T. Davidson.

R. K. Sadhir and H. E. Saunders, "Deposition of Conducting Thin Films of Organometallic Monomers by Plasma Polymerization," J. Vac. Sci, Tech. A3(6) 2093 (1985).

R. K. Sadhir and H. E. Saunders, "Protective Thin Film Coatings by Plasma Polymerization," Semiconductor International 8(3), 110, (1985).

An optical fiber moisture sensor useful in connection with the present invention was prepared by coating a 1 millimeter (mm) diameter quartz rod that was 30 cm in length with a plasma polymerized hexamethyldisiloxane/ammonia film. A tubular plasma polymerization reactor was used for depositing a thin film on the quartz rod substrate. Such reactors are described in the foregoing publications, the disclosures of which are specifically incorporated herein by reference. The quartz rod is placed in the reactor, with one end located approximately 5 cm from the monomer inlet. The conditions used for depositing the film are summarized in Table 1 as follows:

TABLE I

Initial pressure in the reactor = 1.6 Pa
Pressure with ammonia = 4.4 Pa
Flow rate of ammonia = $5.48 \times 10^{-3}$ cm$^3$/sec (STP)
Pressure with hexamethyldisiloxane alone = 7.3 Pa
Flow rate of hexamethyldisiloxane = $4.67 \times 10^{-3}$ cm$^3$/sec (STP)
Total pressure = 10 Pa
Total flow rate = $1.31 \times 10^{-2}$ cm$^3$/sec (STP)
R.F. Power = 20 W
R.R. Frequency = 13.56 MHz
Duration = 6 hours After completing this reaction, the quartz rod was rotated so that the uncoated side was exposed to the plasma. The plasma polymerization was carried out for an additional 5 hours, again under the conditions of Table 1. The resultant coating was estimated to be 1 to 2 um in thickness; however, the thickness was not uniform along the length of the rod.

The rod thus produced was mounted in a flow cell 10 forming a part of a test apparatus 12 utilized to demonstrate the present invention. The test apparatus is illustrated schematically in FIG. 1 where it can be seen that apparatus 12 includes a lamp system 14, a monochromator 16, a photodiode 18 and a photometer 20. The coated quartz rod is identified in FIG. 1 by the reference numeral 11.

Lamp system 14 consists of a Kratos (Schoeffel Instruments) 1000 watt mercury/xenon arc lamp system which includes a lamp 22, a mirror 24 and a condensor lens system 26. The Kratos lamp system is commercially available and the details are known to those of ordinary skill in the art to which the present pertains. Accordingly, further description is not believed necessary.

The light emitted by lamp system 14, which is illustrated by dashed lines 28 in FIG. 1, is passed through a monochromator 16 which comprises a high intensity grating monochromator with wavelength scanning attachments. Again, such monochromators are commercially available (Kratos GM 252, Schoeffel Instruments) and further description is not necessary.

Light from the output slit of monochromator 16 is directed into the input end 11a of the quartz rod 11 mounted in flow cell 10. The output end 11b of probe 11 is coupled directly into the housing of photodiode 18 which includes a photomultiplier tube. High voltage for the photomultiplier tube of photodiode 18 is provided by a photometer 20 (Pacific Precision Instruments, model 110) which also is operable to convert the photomultiplier current output to a voltage. A digital oscilloscope (Nicolet, model 4094) may be used to collect data for experiments where the photomultiplier output is monitored as a function of time or of spectral wavelength.

The details of the construction of flow cell 10 are illustrated in FIG. 2. FIG. 2 illustrates the output end of the flow cell; however, the two ends are essentially the same. Cell 10 comprises an elongated, cylindrical, hollow body 30 which may, for example, be made up of ¼ inch stainless steel tubing. The tubing is provided, at each end, with a tee shaped connector 32. A piece of soft tubing 34 is connected to connector 32 utilizing a luer 36 and a luer adaptor 38. An adaptor 40 is associated with connector 32 as illustrated in FIG. 2 to facilitate passage of the end 11b of probe 11 out of the flow cell. The entrance end of flow cell 10 is of essentially the same construction as illustrated in FIG. 2 and also includes a tee shaped connector 42, as illustrated in FIG. 1.

For demonstration purposes, flow cell 10 was supplied with nominally dry air. The air was alternately directed through a water bath to provide moist air at an estimated 80% relative humidity or bypassed around the water bath to provide a dry environment for testing the fiber-optic probe 11. The results of the tests are illustrated in FIGS. 4, 5 and 6.

Figure 4:
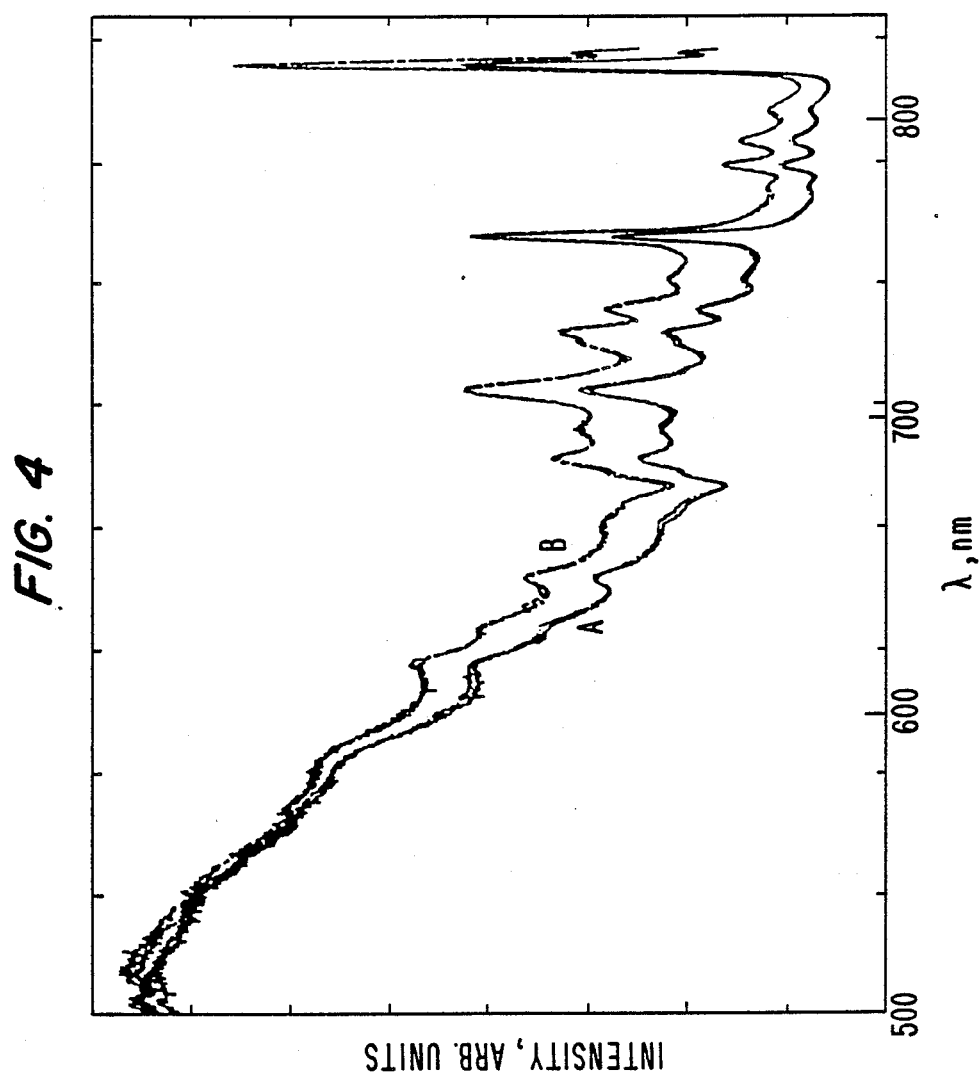

FIG. 4 shows the results of four spectral scans over the range 500 <λ<830 nm. The runs were made with the air in flow tube 10 alternating between dry and moist (in the order dry, moist, dry, moist). The narrow features in the spectra are the emission lines of the lamp, since this apparatus is, in effect, a single beam spectrometer. The sharp lines are useful for internal confirmation of wavelength. The vertical shift between dry (the lower traces, A) and moist (the upper traces, B) is the feature of interest. Increasing absorption by the coating on the sensor rod causes less transmission at the output, and thus a smaller voltage in the photometer output. Thus, the dry form of the film absorbs more strongly than the moist form. The overall decrease in signal, as wavelength increases from 500 nm to greater than 800 nm, is due mainly to the decreasing quantum efficiency of the photomulplier tube and it is theorized that for observation at such long wavelengths, a silicon photodiode might be more suitable.

The agreement between spectra collected under the same condition, after changing from dry to moist to vice versa, indicates that the moisture effect is indeed reversible and quite reproducible.

Figure 5:
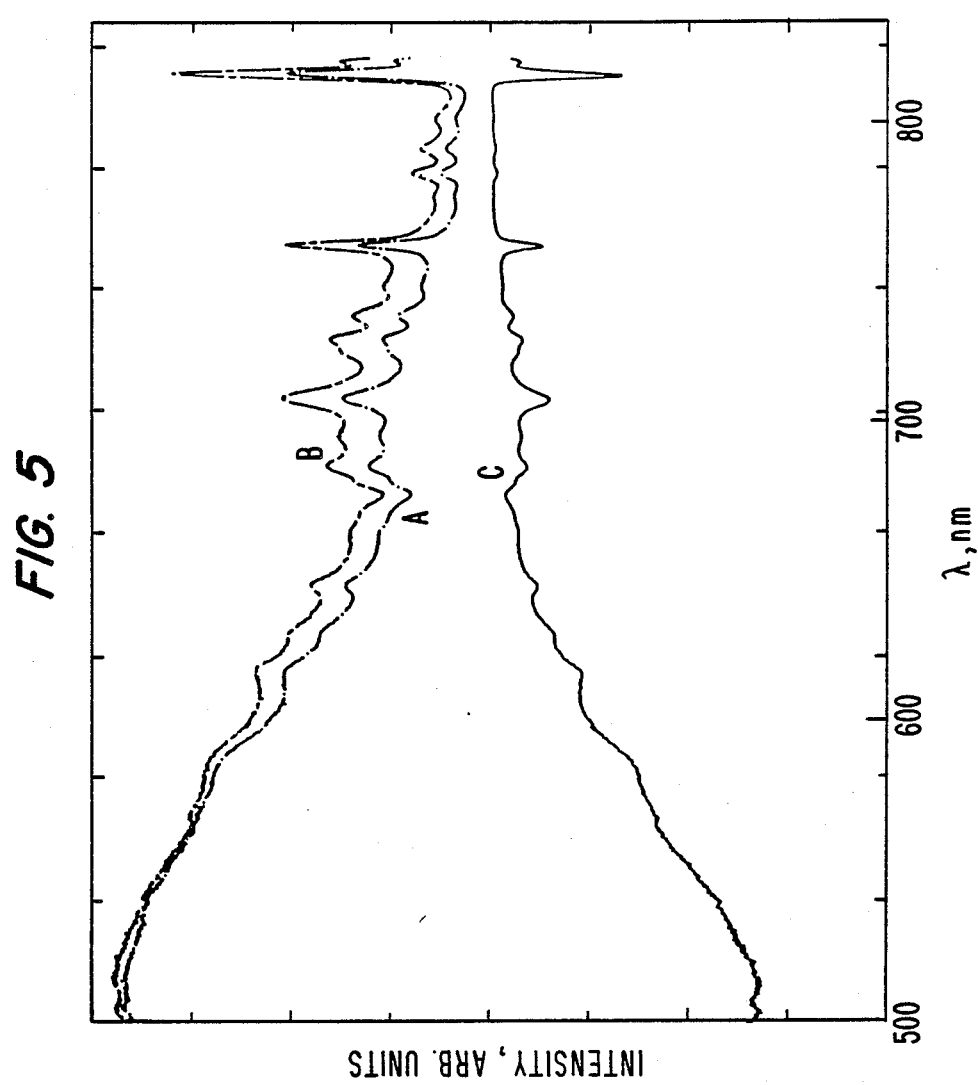

FIG. 5 repeats the spectra under dry (A) and moist (B) conditions and shows the ratio (C) between the two curves. The ratio shows that the available signal, which is the degree of modulation on the transmitted light intensity caused by changes in the moisture level of the surroundings, is greatest at long wavelengths, and becomes essentially independent of wavelength for $\lambda > 700$ nm, and continues out to $\lambda = 820$ nm. 820 nm is a very desirable operating wavelength because commercial optical fibers have a minimum transmission loss at that wavelength, and light sources and detectors for communication systems have been optimized for operation at that wavelength.

FIG. 6 illustrates the transient responses from moist to dry and dry to moist air. The moist to dry transition is complete within approximately 20 seconds. The dry to moist occurs largely within a comparable time, followed by a slower return to the final equilibrated value.

At the scale expansion of FIG. 6, the noise caused by the lamp is quite apparent. The Kratos lamp, which was used for the illustrative testing described above has a noisy intensity output. On the other hand, an optimized system would preferably utilize a stabilized source. Lines B and C of FIG. 6 illustrate the results obtained by averaging 100 sweeps, under fixed conditions, at a fast sweep speed of 250 usec/div. A large noise reduction is observed and the reduced noise curves are indicative of the dynamic range that would be available with a stabilized light source and optimized detection system is used.

Figure 3:
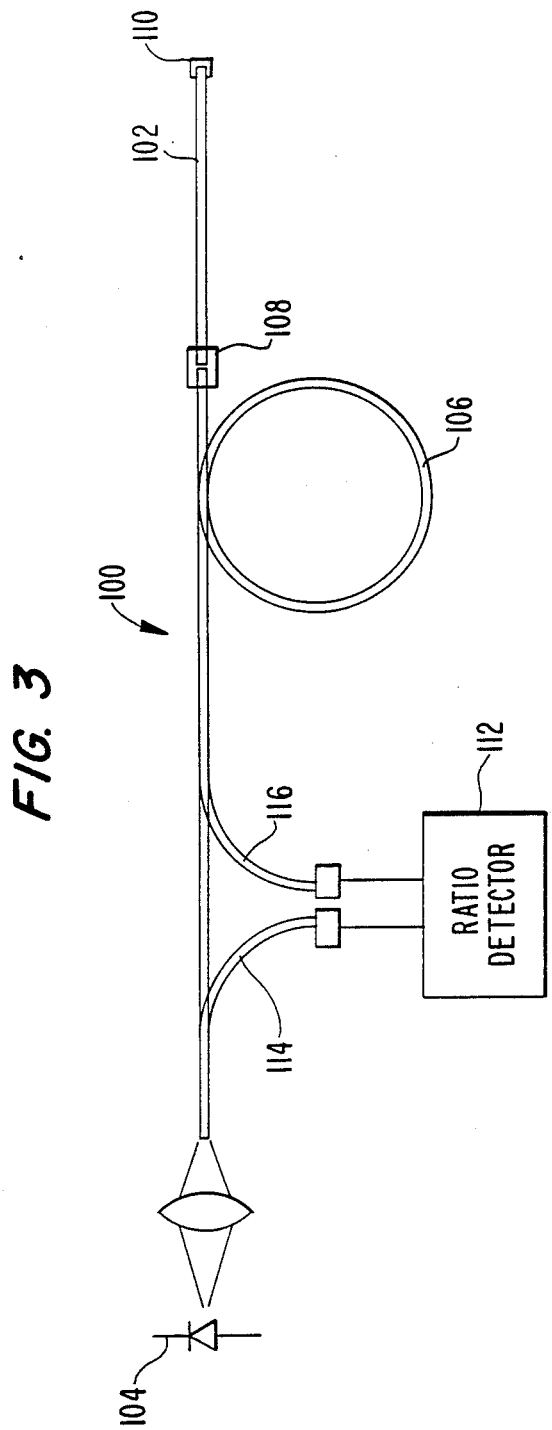
FIG. 3 is a schematic view illustrating the optical system of a preferred embodiment of the fiber-optic moisture sensor of the invention.

The results of testing utilizing the simplified apparatus of FIGS. 1 and 2 led to the optimized fiber-optic moisture sensor illustrated schematically in FIG. 3 and referred to there by the reference numeral 100. The sensor 100 consists of a moisture sensitive optical fiber probe 102 which is adapted to be mounted in an environment where changes in moisture conditions are to be sensed. The sensor includes a light emitting diode (or a diode laser) 104, which provides a stabilized light source operating at 820 nm. Preferably the light source should be pulsed, or chopped, to permit synchronous detection, to thus minimize the effects of stray light sources. Manifestly, diode 104 comprises means for emitting light transmitted through fiber 102.

The light emitted from photodiode 104 is carried to a high quality communications-grade optical fiber 106 which is of arbitrary length to permit the moisture sensitive optical fiber 102 to be located at a considerable distance from the rest of the system. A standard optical fiber connector 108 is provided for connecting the moisture sensitive optical fiber 102 to the communications-grade optical fiber 106.

Moisture sensitive optical fiber 102 may preferably comprise a standard optical fiber core which has a diameter in the range of from about 100 to about 1000 um and a length which ranges from about 10 to about 100 cm.

The distal end 110 of moisture sensitive optical fiber 102 is mirrored to reflect light at 820 nm. Thus, light introduced into the moisture sensitive optical fiber 102 through the optical coupler 108 makes a double pass due to reflection at the mirrored end, and returns through coupler 108 and fiber 106 to a ratio detector 112.

In accordance with the invention, moisture sensitive optical fiber 102 preferably comprises a quartz rod coated with a plasma polymerized coating having a thickness in the range from about 1 to about 10 um. Preferably the coating is deposited on the quartz rod substrate by plasma polymerization from a mixture of hexamethyldisiloxane and ammonia. Such coating is capable of undergoing a color change depending upon the degree of moisture in the surrounding air, with the maximum relative change coming at long wavelengths greater than 700 nm, and in particular permitting operation at the 820 nm wavelength which is conventionally used in optical fiber communication systems. Such an optical moisture sensor should be applicable for determining moisture content in electrically noisy environments such as electrical transformers and generators. And it has been shown by experimentation, the results of which are set forth in FIGS. 4 and 5, that moisture content in a remote environment may be sensed by placing a moisture sensitive optical fiber in the environment, causing light to be transmitted through the fiber and detecting changes in the transmitted light through the fiber as a function of changes in the moisture conditions in the environment.

In the preferred embodiment illustrated in FIG. 3, the portion of the light emitted by photodiode 104 is shunted through shunt fiber leg 114 into ratio detector 112 where it is compared with light returning from the sensor 102 and directed into ratio detector 112 through shunt fiber leg 116. Ratio detector 112 simply compares the intensity of the spectra of the light introduced through shunt leg 114 with the intensity of the light returning from the moisture sensor 102 and introduced into the ratio detector 112 through shunt leg 116. Manifestly, the light entering detector 112 through shunt leg 114 will have an intensity which is different than the intensity of the light returning from sensor 102 through shunt leg 116.

We claim:

1. A method for sensing changes in moisture condition in a fluid environment comprising:
    placing an optical fiber having a moisture sensitive coating thereon in a fluid environment where changes in moisture conditions are to be sensed, said coating being capable of undergoing a change in its light absorption properties depending upon the degree of moisture in the fluid environment;

causing light to be transmitted through said fiber; and detecting changes in the spectra of the light transmitted through the fiber as a function of changes in the moisture conditions in the environment.

2. A method as set forth in claim 1, wherein said step of causing light to be transmitted comprises emitting light from a stabilized light source.

3. A method as set forth in claim 2, wherein said transmitted light is emitted from the light source at a wave length greater than 700 nm.

4. A method as set forth in claim 3, wherein said transmitted light is emitted from the light source at a wave length of 820 nm.

5. A method as set forth in claim 2, wherein said transmitted light is pulsed, or chopped to permit synchronous detection.

6. A method as set forth in claim 2, wherein said light is reflected so as to make a double pass through the fiber prior to said detection step.

7. An optical fiber moisture sensor comprising:

an optical fiber; and a coating on said fiber capable of undergoing a change in its light absorption properties depending upon the degree of moisture in a surrounding fluid environment to thereby alter the optical transmission characteristics of the fiber as a function of the moisture conditions in an environment to which the coating is exposed.

8. An optical fiber moisture sensor as set forth in claim 7, wherein said coating is a polymeric coating.

9. An optical fiber moisture sensor as set forth in claim 8, wherein said polymeric coating is a plasma polymerized coating.

10. An optical fiber moisture sensor as set forth in claim 7, wherein said sensor further comprises a mirrored end on said fiber.

11. Apparatus for sensing changes in moisture conditions in an environment comprising:

a moisture sensitive optical fiber capable of modulating light passing therethrough by absorption and of undergoing a change in its light absorption properties depending upon the degree of moisture in a surrounding fluid environment, said fiber being adapted for being mounted in an environment where changes in moisture conditions are to be sensed;

means for emitting light to be transmitted through said fiber; and means for detecting changes in the spectra of the transmitted light.

12. Apparatus as set forth in claim 11, wherein said moisture sensitive optical fiber comprises a transparent substrate and a coating on the substrate, said coating being capable of undergoing a change in its light absorption properties depending upon the degree of moisture in the fluid environment.

13. Apparatus as set forth in claim 12, wherein is provided a mirrored end for said fiber so that light transmitted light makes a double pass through the fiber.

14. Apparatus as set forth in claim 12, wherein said substrate is a fiber core which is 100 to 1000 um in diameter and 10 to 100 cm in length.

15. Apparatus as set forth in claim 12, wherein said coating is a polymeric coating.

16. Apparatus as set forth in claim 11, wherein said means for emitting light comprises a stabilized light source.

17. Apparatus as set forth in claim 16, wherein said light source emits pulsed or chopped light.

18. Apparatus as set forth in claim 16, wherein said light source emits light at a wave length greater than 700 nm.

19. Apparatus as set forth in claim 18, wherein said light source emits light at a wave length of 820 nm.

20. A method for sensing changes in moisture conditions in a fluid environment comprising:

providing an optical fiber which has been coated with a moisture sensitive coating by plasma polymerization of hexamethyldisiloxane and ammonia onto the surface thereof;

placing said coating optical fiber in a fluid environment where changes in the moisture are to be sensed;

causing light to be transmitted through said fiber; and detecting changes in the light transmitted through the fiber as a function of changes in the moisture conditions in the environment.

21. An optical fiber moisture sensor comprising:

an optical fiber; and a coating on said fiber capable of altering the optical transmission characteristics of the fiber as a function of moisture conditions in an environment to which the coating is exposed, said coating comprising a plasma polymerized polymeric coating made by plasma polymerization of hexamethyldisiloxane and ammonia.

22. Apparatus for sensing changes in moisture conditions in an environment comprising:

a moisture sensitive optical fiber adapted for being mounted in an environment where changes in moisture conditions are to be sensed, said moisture sensitive optical fiber comprising a transparent substrate and a polymeric coating thereon made by plasma polymerization of hexamethyldisiloxane and ammonia on the substrate;

means for emitting light to be transmitted through said fiber; and means for detecting changes in the transmitted light.

23. Apparatus as set forth in claim 22, wherein said substrate is a fiber core which is 100 to 1000 um in diameter and 10 to 100 cm in length and said coating has a thickness of 1 to 10 um.

* * * * *